United States Patent
Anton et al.

(10) Patent No.: US 11,918,989 B2
(45) Date of Patent: Mar. 5, 2024

(54) PROCESS FOR REGENERATION OF HYDROGENATION CATALYSTS

(71) Applicant: Evonik Operations GmbH, Essen (DE)

(72) Inventors: Johan Anton, Dorsten (DE); Michael Grass, Haltern am See (DE); Johannes Kraft, Niederkassel (DE); Thomas Schneider, Schermbeck (DE); Grzegorz Ziomek, Recklinghausen (DE)

(73) Assignee: Evonik Operations GmbH, Essen (DE)

(*) Notice: Subject to any disclaimer, the term of this patent is extended or adjusted under 35 U.S.C. 154(b) by 138 days.

(21) Appl. No.: 17/547,330

(22) Filed: Dec. 10, 2021

(65) Prior Publication Data
US 2022/0193653 A1    Jun. 23, 2022

(30) Foreign Application Priority Data
Dec. 18, 2020   (EP) .................................... 20215552

(51) Int. Cl.
*B01J 38/04*   (2006.01)
*B01J 38/02*   (2006.01)

(52) U.S. Cl.
CPC ............ *B01J 38/04* (2013.01); *B01J 38/02* (2013.01)

(58) Field of Classification Search
CPC ........ B01J 21/063; B01J 23/462; B01J 23/94; B01J 23/96; B01J 35/008; B01J 38/02; B01J 38/04; B01J 38/12; C07C 67/303; C07C 2601/14; Y02P 20/582
See application file for complete search history.

(56) References Cited

U.S. PATENT DOCUMENTS

| | | | |
|---|---|---|---|
| 5,030,609 A * | 7/1991 | Turner | B01J 23/868 502/318 |
| 7,361,714 B2 | 4/2008 | Grass et al. | |
| 7,388,119 B2 | 6/2008 | Bottcher et al. | |
| 8,598,060 B2 | 12/2013 | Henkelmann et al. | |
| 8,895,791 B2 | 11/2014 | Henkelmann et al. | |
| 10,501,392 B2 | 12/2019 | Fridag et al. | |
| 10,787,414 B2 | 9/2020 | Boeck et al. | |
| 2011/0144398 A1 | 6/2011 | Mirk et al. | |
| 2021/0179534 A1 | 6/2021 | Schulz et al. | |

FOREIGN PATENT DOCUMENTS

| | | |
|---|---|---|
| WO | 03/010119 A1 | 2/2003 |
| WO | 03/103830 A1 | 12/2003 |
| WO | 2008/015103 A2 | 2/2008 |
| WO | 2008/015135 A2 | 2/2008 |

OTHER PUBLICATIONS

European Search Report dated May 21, 2021 in EP 20215552.9 (7 pages).
König et al., "Influence of the support on sulfur poisoning and regeneration of Ru catalysts probed by sulfur K-edge X-ray absorption spectroscopy," Catalysis Today, Elsevier, Amsterdam, NL, Bd. 229, Copyright 2013, pp. 56-63 (7 pages).
Klostermann et al., U.S. Appl. No. 17/543,261, filed Dec. 6, 2021.

* cited by examiner

*Primary Examiner* — Brian A McCaig
(74) *Attorney, Agent, or Firm* — Grüneberg and Myers, PLLC

(57) ABSTRACT

The invention provides a process for regenerating a catalyst used for the hydrogenation of an aromatic species, consisting of several steps. First the system is purged with nitrogen, then air is metered in stepwise, and the addition of nitrogen is subsequently ended until only air is present.

20 Claims, No Drawings

PROCESS FOR REGENERATION OF HYDROGENATION CATALYSTS

CROSS REFERENCE TO RELATED APPLICATIONS

This application is a 35 U.S.C. § 119 patent application which claims the benefit of European Application No. 20215552.9 filed Dec. 18, 2020, which is incorporated herein by reference in its entirety.

The present invention relates to a process for regenerating a catalyst used for the hydrogenation of an aromatic species, consisting of several steps. First the system is purged with nitrogen, then air is metered in stepwise, and the addition of nitrogen is subsequently ended until only air is present.

BACKGROUND

The hydrogenation of aromatic species, especially of aromatic esters, in which the aromatic ring is hydrogenated, is known and is also referred to as ring hydrogenation. In such a hydrogenation, for example, transition metal-containing catalysts are used. Suitable catalysts are known to those skilled in the art. Corresponding hydrogenation processes are also used on an industrial scale.

With increasing duration of hydrogenation, the catalysts used can lose activity, whether as a result of blocking, loss or poisoning of the active sites of the catalyst. If the loss of activity is too high and/or the hydrogenation process can no longer be operated economically, the activity of the catalyst must be increased. This is accomplished by means of a regeneration process in which the catalyst is freed of deposited and adhering matter. It is possible here to calcine the catalyst, in which the deposits are removed at high temperatures (>200° C.) under air or in an inert gas atmosphere, but this can be problematic for particular catalysts or else purely for energy reasons on account of the high temperatures.

Catalysts can alternatively be regenerated by passing a gas stream over them, by which the deposits are entrained and hence removed. Such a process for regeneration of ruthenium catalysts is described, for example, in WO 2008/015103 A1. It is a feature of the regeneration disclosed therein that the catalyst is purged with an inert gas until the catalyst has partly or even completely regained its activity. A reason given for the regenerating action described with reference to benzene hydrogenation is the removal of water, i.e. the drying of the catalyst.

However, the known process has the problem that the regenerating effect can be too small, especially when not just water has to be removed from the catalyst, or not just water but also other substances that lower the hydrogenation activity are present on the catalyst.

Accordingly, the problem addressed by the present invention was that of providing processes for regenerating a catalyst used for the ring hydrogenation of an aromatic species, especially an aromatic ester, with which an acceptable activity can be achieved better and more quickly.

SUMMARY

This problem is solved by the process set forth herein. Preferred embodiments are specified in the dependent claims. The process according to the invention is a process for regenerating a catalyst used for the ring hydrogenation of an aromatic species, preferably for ring hydrogenation of an aromatic ester, in at least one reactor, wherein the process comprises the following steps:

purging the at least one reactor in which the catalyst used is present with an inert gas, wherein the purging with an inert gas, preferably with nitrogen, is commenced at a temperature of 50 to 100° C.; followed by stepwise addition of air to the inert gas during the purging of the reactor until the proportion of air in the total volume is between 10% and 90% by volume; and then a reduction in the amount of inert gas, preferably in the amount of nitrogen, during the purging of the reactor until only air is flowing through the reactor, wherein the temperature in the reactor during the regeneration is not more than 10° C. higher than the temperature at the reactor feed for the aromatic species, preferably aromatic ester, in the hydrogenation of the aromatic species, preferably of the aromatic ester, wherein the catalyst comprises at least one transition metal selected from the group consisting of iron, ruthenium, nickel, rhodium, platinum, palladium and mixtures thereof, on a support material selected from the group consisting of activated carbon, silicon carbide, aluminium oxide, silicon dioxide, aluminosilicate, titanium dioxide, zirconium dioxide, magnesium oxide, zinc oxide and mixtures thereof.

DETAILED DESCRIPTION

The process according to the invention can achieve advantageous regeneration of the hydrogenation catalyst, by which the catalyst activity is improved very easily and rapidly. The regeneration described here thus enables subsequent restarting of the ring hydrogenation, by which the actual products of value are produced, at increased conversions and hence more effective performance. At the same time, the comparatively low oxygen concentration or the correspondingly controlled process sequence prevents excessively elevated temperatures (possibly even only locally) from occurring in the reactor as a result of oxidation processes, which can damage the catalyst or in the worst case lead to reactor damage.

The ring hydrogenation of aromatic species described here, especially of aromatic esters, is typically conducted in at least one reactor, meaning that the ring hydrogenation can be effected in one or more reactors each containing a suitable catalyst. The inventive regeneration of the catalyst used can be effected in any of the reactors present. In the case of presence of multiple reactors, the regeneration can be effected at different times or simultaneously for each reactor, preference being given to simultaneous regeneration of all catalysts in all the reactors present. It is therefore an advantage of the invention that the catalyst, for the regeneration, does not need to be taken out of the reactor, but can remain in the reactor in which the ring hydrogenation also takes place.

According to the invention, the process is suitable for all catalysts used in the ring hydrogenation of aromatic species, especially of aromatic esters. The catalyst comprises at least one transition metal on a support material, or consists of at least one transition metal on a support material. Suitable catalysts are also familiar to the person skilled in the art and can be found, for example, in WO 03/103830 A1.

The transition metal of the catalyst to be regenerated is a metal selected from the group consisting of iron, ruthenium, nickel, rhodium, platinum, palladium and mixtures thereof. Ruthenium is the transition metal for the catalyst used which is particularly preferred in the present invention. The content of transition metal in the catalyst to be generated is generally 0.1% to 30% by mass. The ruthenium content, calculated as the metal, is preferably in the range from 0.1% to 10% by mass, especially in the range from 0.3% to 5% by mass, very particularly in the range between 0.4% and 2.5% by mass.

The support material on which the transition metal is present is selected from the group consisting of activated carbon, silicon carbide, aluminium oxide, silicon dioxide, aluminosilicate, titanium dioxide, zirconium dioxide, magnesium oxide, zinc oxide and mixtures thereof. Preferred support materials are aluminium oxide, silicon dioxide, titanium dioxide and mixtures thereof. In addition, these support materials may comprise alkali metals, alkaline earth metals and/or sulfur. In a particularly preferred embodiment of the present invention, the catalyst to be regenerated is an eggshell catalyst.

The process according to the invention for regeneration of a catalyst used for the ring hydrogenation of an aromatic species, preferably for ring hydrogenation of an aromatic ester, comprises three steps. These steps are effected in the at least one reactor, and they are accordingly conducted without deinstalling the catalyst. In the three steps, gas streams having different composition according to the current step are guided through the reactors in which the catalysts are present. This frees the catalyst of the possible deposited and adhering matter.

In the first step, an inert gas is passed through the reactor(s) and hence purges them. The inert gas here may be selected from the group consisting of nitrogen, helium, neon, argon, carbon dioxide and mixtures thereof. Preference is given to using nitrogen or carbon dioxide since these are the most readily and cheaply available. More preferably, nitrogen is the inert gas for the process according to the invention.

Temperature is an important feature of the present invention. For instance, the temperature in the reactor during the regeneration must not be more than 10° C. higher than the temperature at the reactor feed for the aromatic ester in the hydrogenation of the aromatic ester. Burnoff of the catalyst or calcination of the catalyst, which can be brought about by a possibly extreme temperature rise caused by the addition of atmospheric oxygen, is thus to be prevented by the teaching of the invention. According to the invention, the temperature in the reactor can be measured at any desired position within the reactor. The first step, i.e. the purging with an inert gas, preferably the purging with nitrogen, is commenced at a temperature of 50 to 100° C. Since the temperature in the ring hydrogenation that precedes the regeneration may be higher than 100° C., it may be necessary to cool the reactor prior to the regeneration, for example by simply leaving it to stand or by actively cooling with passage of the hydrogenation product through a cooler.

It is preferable that the temperature falls with time during the regeneration. However, the subsequent steps can result in temporary, brief rises in temperature. It should nevertheless be possible to detect a drop in the temperature over time, since the reactors or gas streams are not being specifically heated.

Prior to the first step, the purging of the reactor with inert gas, preferably nitrogen, and after shutdown of the hydrogenation, it is possible to conduct further steps. Preference is given to conducting the following steps:
  decompressing the at least one reactor to a pressure of less than 10 bar, preferably less than 7.5 bar, more preferably less than 5 bar;
  displacing the remaining hydrogen from the at least one reactor by injecting an inert gas, preferably nitrogen, to a pressure of more than 10 bar, preferably more than 12.5 bar, more preferably more than 15 bar, and then
  decompressing the at least one reactor to a pressure of less than 10 bar, preferably less than 7.5 bar, more preferably less than 5 bar.

The sequence of injecting of an inert gas, preferably of nitrogen, and subsequent decompression is conducted at least twice in a preferred embodiment. This is then followed by the first step of the regeneration process according to the invention, i.e. the purging with inert gas.

In the second step of the regeneration process according to the invention, air is added stepwise to the inert gas during the purging of the reactor(s) until the proportion of air in the total volume is between 10% and 90% by volume, preferably between 20% and 80% by volume, more preferably between 20% and 60% by volume. The stepwise addition of air is preferably effected in at least 3 steps, with only the last step providing the abovementioned proportion of air. The addition of air guides oxygen into the system, which can lead to oxidation reactions and hence to a local rise in temperature. It is therefore advisable to monitor the temperature in the at least one reactor, for example with suitable measurement sensors. It may be advantageous that multiple measurement sensors are present in the at least one reactor in order that temperature rises that occur locally can also be detected.

In a preferred embodiment, the temperature in the second step, more preferably also temporarily, during a step of the stepwise addition of air, is not more than 20° C., more preferably not more than 15° C., higher than on commencement of the same respective step of the stepwise addition of air. The air is added here in a controlled manner, which prevents burnoff of the catalyst and/or excessive oxidation of the catalyst. If a higher temperature should nevertheless arise, even locally, it is advisable to initiate countermeasures. Preferably in accordance with the invention, the (further) addition of air is stopped at least temporarily when the temperature during a step of the stepwise addition of air is 20° C., preferably 15° C. or more, above the temperature on commencement of the same respective step of the stepwise addition of air. It is also possible that inert gas, preferably nitrogen, is additionally metered in during the stoppage of the further addition of air.

It is a feature of the third step of the regeneration process according to the invention that the amount of inert gas, preferably the amount of nitrogen, is reduced stepwise during the purging of the reactor until only air is flowing through the reactor. This step can be effected either only after the second step has ended or partly or completely during the performance of the second step. If there should be a (local) increase in temperature here, temporary stoppage of the reduction in the amount of inert gas or even further metered addition of inert gas, preferably nitrogen, would be possible. The first step, i.e. the flow-through of air, is preferably effected at a temperature of up to 70° C. when the addition of inert gas has been ended completely. The temperature will preferably fall further with time, preferably to ambient temperature, i.e. to a temperature within a range of 20-35° C.

The time for which the regeneration described in the present context has to be conducted in order to improve the catalyst activity to a sufficient degree depends on various factors. Examples of these factors are the nature and amount of the impurities, or the characteristics of the reactors (size, diameter). The duration of the overall regeneration, i.e. the performance of all steps, is preferably at least 24 hours, more preferably at least 3 days. In the case of shorter times, the plant can be restarted more quickly. However, the regeneration in that case is not as extensive, and it may be the case that a new regeneration is soon required.

The gas streams in the individual steps of the process according to the invention are preferably guided through the reactor or over the catalyst at a volume flow rate of at least 2 m$^3$ per m$^3$ of catalyst per hour. Such volume flow rates enable comparatively rapid regeneration. The gas stream in the individual steps of the regeneration may be guided over the catalyst in the same or in the reverse flow direction, based on the flow direction in the hydrogenation; this is preferably done in the same flow direction.

The regeneration according to the invention is effected in the case of a catalyst used in the ring hydrogenation of an aromatic species. In a preferred embodiment, the regeneration according to the invention is effected in the case of a catalyst used in the ring hydrogenation of an aromatic ester. The aromatic ester is preferably an ester of a benzenecarboxylic acid, an ester of a benzenedicarboxylic acid, an ester of a benzenetricarboxylic acid or an ester of a benzenetetracarboxylic acid, preferably an ester of benzenedicarboxylic acid or of benzenetricarboxylic acid. These include phthalates, isophthalates, terephthalates and trimellitates. Preference is given to esters of benzenedicarboxylic acid, i.e. phthalates, isophthalates and terephthalates. Among these, preference is given particularly to the C8- to C10-alkyl esters, especially the C8- to C10-alkyl esters of phthalic acid (e.g. dioctyl phthalate, diethylhexyl phthalate, diisononyl phthalate, dipropylheptyl phthalate) or the C8- to C10-alkyl esters of terephthalic acid (e.g. dioctyl terephthalate, diethylhexyl terephthalate, diisononyl terephthalate, dipropylheptyl terephthalate).

The ring hydrogenation is preferably conducted in the liquid phase. The ring hydrogenation can be conducted continuously or batchwise over suspended catalysts or those arranged in piece form in a fixed bed. In the process according to the invention, preference is given to continuous ring hydrogenation over a catalyst in fixed bed form, in which the product/reactant phase is mainly in the liquid state under the reaction conditions. Preference is given to operating the reactor(s) as a trickle bed reactor that may be completely or partly flooded.

If the ring hydrogenation is conducted continuously over a catalyst in fixed bed form, it is advantageous to convert the catalyst to the active form prior to the first performance of the ring hydrogenation. After a regeneration, such an activation is not absolutely necessary. The activation can be effected by reduction of the catalyst using hydrogen-containing gases according to a temperature programme. The reduction here can optionally be performed in the presence of a liquid phase that trickles over the catalyst. The liquid phase used here may be a solvent or the hydrogenation product. Given corresponding hydrogenation conditions, it is also possible to dispense with such an activation, since this is also effected under reaction conditions.

Various process variants may be chosen for the ring hydrogenation. It may be performed under adiabatic, polytropic or virtually isothermal conditions, i.e. with a temperature rise of typically less than 10° C., in one or more stages. In the latter case, all reactors, appropriately tubular reactors, may be operated adiabatically or virtually isothermally, or else one or more adiabatically and the others virtually isothermally. It is additionally possible to hydrogenate the aromatic polycarboxylic esters in straight pass or with product recycling. It is also possible that two reactors are present, in which case the first reactor is operated with product recycling and the second reactor in straight pass. Another option is performance of the ring hydrogenation as a trickle bed. The reactor here may also be partly or fully flooded. In addition, it is also possible to use more than two reactors. It would be particularly preferable in this case too for all the reactors except for the last one to be operated with product recycling ("loop reactor") and only the last one in straight pass.

The ring hydrogenation may be conducted in cocurrent in a liquid/gas mixed phase or in the liquid phase in triphasic reactors, with the hydrogenation gas distributed in the liquid reactant/product stream in a manner known per se. In the interests of a uniform liquid distribution, of improved removal of heat of reaction and of a high space-time yield, the reactors are preferably operated with high liquid loads of 15 to 120, especially of 25 to 80, m$^3$ per m$^2$ of cross section of the empty reactor and per hour. When a reactor is operated in straight pass, the specific liquid hourly space velocity (LHSV) may assume values between 0.1 and 10 h$^{-1}$.

The ring hydrogenation can be conducted in the absence or preferably in the presence of a solvent. The solvent used may be all liquids that form a homogeneous solution with the reactant and product, are inert under hydrogenation conditions and can be easily removed from the product. The solvent may also be a mixture of two or more substances and may optionally comprise water.

For example, it is possible to use the following substances as solvent:straight-chain or cyclic ethers such as tetrahydrofuran or dioxane and also aliphatic alcohols in which the alkyl radical has 1 to 13 carbon atoms. Alcohols usable with preference are, for example, isopropanol, n-butanol, isobutanol, n-pentanol, 2-ethylhexanol, nonanols, technical nonanol mixtures, decanol, technical decanol mixtures, tridecanols.

When alcohols are used as solvent, it may be appropriate to use that alcohol or that alcohol mixture that would form in the hydrolysis of the product. This rules out by-product formation through transesterification. A further preferred solvent is the hydrogenation product itself.

The use of a solvent allows the aromatic species concentration in the reactor feed to be limited, as a result of which better temperature control in the reactor can be achieved. This can minimize side reactions and accordingly bring about an increase in product yield. The aromatic species content in the reactor feed is preferably between 1% and 35%, especially between 5% and 25%. The desired concentration range in the case of reactors that are operated in loop mode can be adjusted via the circulation rate (ratio of hydrogenation output recycled to reactant).

The ring hydrogenation can be conducted within a pressure range from 20 to 300 bar, preferably 40 to 200 bar. The hydrogenation temperatures are preferably in the range from 60° C. to 200° C., especially in the range from 80° C. to 180° C.

Hydrogenation gases used may be any desired hydrogen-containing gas mixtures that do not contain harmful amounts of catalyst poisons, for example carbon monoxide or hydrogen sulfide.

The inert gas constituents may, for example, be nitrogen or methane. Preference is given to using hydrogen in a purity of greater than 95%, especially greater than 98%.

The invention is elucidated hereinafter by examples. These examples disclose exemplary embodiments and should not be regarded as limiting.

Example 1

The process according to the invention was tested in an industrial scale plant. A ring hydrogenation of diisononyl phthalate (DINP) was conducted beforehand. The hydrogen needed for the hydrogenation was taken from the existing site grid and compressed to the requisite reaction pressure with a compressor. The hydrogenation is effected in the first reactor under a reaction pressure of about 100 bar and at a reaction temperature of about 110° C. over a fixed bed catalyst (1% Ru on $TiO_2$ as support material). The DINP was converted in the reactor down to a residual concentration of about 10%. The process is conducted with two reactors: a main reactor and a postreactor. The main reactor is operated as an adiabatic circulation reactor. The heat of reaction formed by the exothermic hydrogenation is removed by circulating a large circulation stream with a pump from the bottom of the main reactor and back to the top of the main reactor via an air cooler. Beyond the cooler, the reactant stream is metered into the circulation stream and, before it enters the main reactor, the desired temperature is established by closed-loop control of the circulation stream temperature. A discharge from the circulation stream of the main reactor is guided to the postreactor. The remaining about 10% DINP in the discharge stream from the main reactor is hydrogenated down to <100 ppm in the postreactor under reaction conditions similar to those in the main reactor.

Subsequently, the reactors were first inertized. For this purpose, the reactors were decompressed down to about 3 bar and then there were three cycles of injection of nitrogen to about 20 bar and decompression again, in order to displace residual nitrogen from the reactors.

This was followed by regeneration. Regeneration was commenced at a reactor temperature of about 60 to 90° C. in the feed. For this purpose, main reactor and postreactor were purged separately with nitrogen. The amount of nitrogen was adjusted such that the pressure drop over the respective reactors was <0.1 bar, corresponding to about 5 m³ (STP) per hour and per m³ of catalyst material for the main reactor and about 15 m³ (STP) per hour and per m³ of catalyst material for the postreactor. After 3 to 6 hours, air was added stepwise in 4 steps over the course of 21 hours until the proportion of air in the gas stream was about 50% of the volume flow rate. Subsequently, at reactor temperatures in the range from 15 to 70° C., the addition of nitrogen was reduced correspondingly in 2 steps over the course of 7 hours until only air was flowing through the reactors. In all steps it was ensured that the temperature in the reactor did not rise by 10° C. with respect to the feed temperature, in order to avoid burnoff of the catalyst by the atmospheric oxygen. The flow of air was maintained for several more days.

Before and after the reaction, the rate constant of the hydrogenation was ascertained, and this was used to calculate the activity of the catalyst before and after. The rate constant was ascertained from the various measurement data from the plant with the Aspen Plus® simulation software from AspenTech, assuring comparability of the data by a defined feed rate.

In the context of this application, the catalyst activity is determined as the relation of the ascertained rate constant ($k_{current}$) and the theoretical rate constant ($k_{theoretical}$). The catalyst activity is calculated by the following formula:

$$\text{Catalyst activity} = \frac{k_{current}}{k_{theoretical}} \cdot 100\%$$

The results of the experiments are shown in Table 1 below.

TABLE 1

Catalyst activities ascertained after regeneration

| Catalyst activity | Regeneration | |
| --- | --- | --- |
| | before | after |
| Main reactor | 60.6% | 95.3% |
| Postreactor | 15.5% | 38.9% |

It is found that the regeneration according to the invention leads to distinctly higher catalyst activities.

The invention claimed is:
1. A process for regenerating a catalyst used for the ring hydrogenation of an aromatic species, in at least one reactor, wherein the process comprises the following steps:
  purging the at least one reactor in which the catalyst used is present with an inert gas, wherein the purging with an inert gas is commenced at a temperature of from 50 to 100° C.; followed by
  stepwise addition of air to the inert gas during the purging of the reactor until the proportion of air in the total volume is between from 10% and 90% by volume; and then
  a reduction in the amount of inert gas during the purging of the reactor until only air is flowing through the reactor,
  wherein the temperature in the reactor during the regeneration is not more than 10° C. higher than the temperature at the reactor feed for the aromatic species, in the hydrogenation of the aromatic species,
  wherein the catalyst comprises at least one transition metal selected from the group consisting of iron, ruthenium, nickel, rhodium, platinum, palladium, and mixtures thereof, on a support material selected from the group consisting of activated carbon, silicon carbide, aluminium oxide, silicon dioxide, aluminosilicate, titanium dioxide, zirconium dioxide, magnesium oxide, zinc oxide, and mixtures thereof.

2. The process according to claim 1, wherein the temperature in the at least one reactor is monitored during the stepwise addition of air and/or during the reduction in the amount of inert gas.

3. The process according to claim 2, wherein the temperature during the stepwise addition of air is not more than 20° C. higher than on commencement of the respective step of stepwise addition of air.

4. The process according to claim 2, wherein the addition of air is stopped at least temporarily when the temperature during the stepwise addition of air is 20° C. above the temperature on commencement of the respective step of stepwise addition of air.

5. The process according to claim 4, wherein inert gas is metered in during the stoppage.

6. The process according to claim 2, wherein the temperature during the stepwise addition of air is not more than 15° C. higher than on commencement of the respective step of stepwise addition of air.

7. The process according to claim 2, wherein the addition of air is stopped at least temporarily when the temperature during the stepwise addition of air is 15° C. above the temperature on commencement of the respective step of stepwise addition of air.

8. The process according to claim 2, wherein the aromatic species is an aromatic ester.

9. The process according to claim 8, wherein the aromatic ester is an ester of a benzenecarboxylic acid, of a benzenedicarboxylic acid, of a benzenetricarboxylic acid, or of a benzenetetracarboxylic acid.

10. The process according to claim 1, wherein the purging of the at least one reactor with the inert gas is preceded by performance of the following steps:
   decompressing the at least one reactor to a pressure of less than 10 bar;
   displacing any remaining hydrogen from the at least one reactor by injecting an inert gas, to a pressure of more than 10 bar, and then decompressing the at least one reactor to a pressure of less than 10 bar.

11. The process according to claim 10, wherein the injecting of an inert gas and the subsequent decompression is conducted at least twice.

12. The process according to claim 1, wherein the duration for regenerating the catalyst is at least 24 hours.

13. The process according claim 1, wherein the inert gas is selected from the group consisting of nitrogen, helium, neon, argon, carbon dioxide and mixtures thereof.

14. The process according to claim 1, wherein the aromatic species is an aromatic ester.

15. The process according to claim 14, wherein the aromatic ester is an ester of a benzenecarboxylic acid, of a benzenedicarboxylic acid, of a benzenetricarboxylic acid, or of a benzenetetracarboxylic acid.

16. The process according to claim 14, wherein the aromatic ester is a C8- to C10-alkyl ester of phthalic acid or a C8- to C10-alkyl ester of terephthalic acid.

17. The process according to claim 1, wherein the purging of the at least one reactor with the inert gas is preceded by performance of the following steps:
   decompressing the at least one reactor to a pressure of less than 5 bar;
   displacing any remaining hydrogen from the at least one reactor by injecting nitrogen, to a pressure of more than 15 bar, and then decompressing the at least one reactor to a pressure of less than 5 bar.

18. The process according to claim 1, wherein the duration for regenerating the catalyst is at least 3 days.

19. The process according to claim 1, wherein the purging of the at least one reactor with the inert gas is preceded by performance of the following steps:
   decompressing the at least one reactor to a pressure of less than 7.5 bar; and
   displacing any remaining hydrogen from the at least one reactor by injecting nitrogen to a pressure of more than 12.5 bar, and then decompressing the at least one reactor to a pressure of less than 7.5 bar.

20. The process according to claim 19, wherein the injecting of nitrogen, and the subsequent decompression is conducted at least twice.

\* \* \* \* \*